(12) United States Patent
Foley

(10) Patent No.: US 7,625,378 B2
(45) Date of Patent: Dec. 1, 2009

(54) DEVICES AND METHODS FOR SECURING A BONE PLATE TO A BONY SEGMENT

(75) Inventor: Kevin T. Foley, Germantown, TN (US)

(73) Assignee: Warsaw Orthopedic, Inc.

( * ) Notice: Subject to any disclaimer, the term of this patent is extended or adjusted under 35 U.S.C. 154(b) by 578 days.

(21) Appl. No.: 10/261,120

(22) Filed: Sep. 30, 2002

(65) Prior Publication Data

US 2004/0092947 A1    May 13, 2004

(51) Int. Cl.
*A61B 17/58*    (2006.01)
(52) U.S. Cl. ....................... 606/96; 606/86 B
(58) Field of Classification Search ............ 606/96, 606/65, 69–71, 99, 280–299, 914, 915, 86 B, 606/86 A, 902–906
See application file for complete search history.

(56) References Cited

U.S. PATENT DOCUMENTS

| | | | | |
|---|---|---|---|---|
| 3,439,671 A | * | 4/1969 | Kuntscher | 606/96 |
| 3,867,932 A | * | 2/1975 | Huene | 606/80 |
| 4,232,660 A | * | 11/1980 | Coles | 600/210 |
| 4,461,305 A | * | 7/1984 | Cibley | 600/567 |
| 4,945,904 A | * | 8/1990 | Bolton et al. | 606/96 |
| 5,084,049 A | * | 1/1992 | Asher et al. | 606/61 |
| 5,147,367 A | * | 9/1992 | Ellis | 606/96 |
| 5,298,254 A | * | 3/1994 | Prewett et al. | 424/422 |
| 5,423,826 A | * | 6/1995 | Coates et al. | 606/96 |
| 5,669,915 A | * | 9/1997 | Caspar et al. | 606/96 |
| 5,676,666 A | * | 10/1997 | Oxland et al. | 606/61 |
| 5,755,721 A | | 5/1998 | Hearn | |
| D401,335 S | * | 11/1998 | Koros et al. | D24/133 |
| 5,851,207 A | | 12/1998 | Cesarone | |
| 5,885,300 A | * | 3/1999 | Tokuhashi et al. | 606/99 |
| 6,066,142 A | | 5/2000 | Serbousek et al. | |
| 6,193,721 B1 | | 2/2001 | Michelson | |
| 6,193,723 B1 | * | 2/2001 | Cripe et al. | 606/88 |
| 6,235,034 B1 | | 5/2001 | Bray | |
| 6,258,089 B1 | * | 7/2001 | Campbell et al. | 606/61 |
| 6,332,887 B1 | | 12/2001 | Knox | |
| 6,342,056 B1 | | 1/2002 | Mac-Thiong et al. | |
| 6,342,057 B1 | | 1/2002 | Brace et al. | |

(Continued)

FOREIGN PATENT DOCUMENTS

WO    WO 02/080791 A1    10/2002

OTHER PUBLICATIONS

Thomas A. Zdeblick, M.D. and Harry N. Herkowitz, M.D.; Premier Anterior Cervical Plate System, Surgical Technique; Premier Anterior Cervical Plate System; 2000 Medtronic Sofamor Danek.

(Continued)

*Primary Examiner*—Thomas C Barrett
*Assistant Examiner*—James L. Swiger (57) ABSTRACT

A guide assembly for positioning one or more bone engaging fasteners in a bony segment includes at least one guide tube and an extension extending distally from a distal end of the at least one guide tube. The extension is contactable with at least one of the plate and the bony segment with a passage of the guide tube aligned with a bone fastener hole through the plate and the distal end of the guide tube spaced from the plate.

45 Claims, 7 Drawing Sheets

U.S. PATENT DOCUMENTS

| | | |
|---|---|---|
| 6,379,364 B1 | 4/2002 | Brace et al. |
| 6,436,103 B1 | 8/2002 | Suddaby |
| 6,506,151 B2 * | 1/2003 | Estes et al. .................. 600/226 |
| 6,682,535 B2 * | 1/2004 | Hoogland .................... 606/80 |
| 6,692,503 B2 * | 2/2004 | Foley et al. .................... 606/96 |
| 6,793,658 B2 * | 9/2004 | LeHuec et al. ................ 606/61 |
| 6,916,323 B2 * | 7/2005 | Kitchens ...................... 606/86 |
| 6,929,606 B2 * | 8/2005 | Ritland ....................... 600/201 |
| 2001/0047172 A1 | 11/2001 | Foley et al. |
| 2003/0233098 A1 * | 12/2003 | Markworth .................. 606/96 |
| 2004/0015174 A1 * | 1/2004 | Null et al. .................... 606/99 |
| 2005/0143741 A1 * | 6/2005 | Timmermans et al. ........ 606/70 |
| 2006/0142762 A1 * | 6/2006 | Michelson .................. 606/61 |

OTHER PUBLICATIONS

Zephir Anterior Cervical Plate System, Surgical Technique; 2000 Medtronic Sofamor Danek; pp. 1-8.

Gary L. Lowery, MD, PhD; Sugical Technique; Orion Anterior Cervical Plate System; Sofamor Danek The Spine Specialist; pp. 1-24.

* cited by examiner

DEVICES AND METHODS FOR SECURING A BONE PLATE TO A BONY SEGMENT

BACKGROUND

Bony structures are subject to defects and trauma which require a bone plate to be secured thereto in order to stabilize the bony segment as it heals, fuses or is restored. For example, the spine is subject to various pathologies that compromise its load bearing and support capabilities. Such pathologies of the spine include, for example, degenerative diseases, the effects of tumors and fractures and dislocations attributable to physical trauma. The use of bone plates has been helpful in the stabilization and fixation of the spine, including the sacral, lumbar, thoracic, and cervical regions of the spine, as well as other bony segments in the body.

Various instruments and techniques have been developed to prepare the bony segment for receipt of one or more bone engaging fasteners to secure the bone plate thereto. Examples of such instruments include drills, taps, awls, and driving instruments. Devices for guiding such instruments into the bony segment can facilitate positioning of bone engaging fasteners at the desired orientation relative to the bone plate. However, such devices may be difficult or time consuming to secure to the bone plate. Such devices may also have to be removed during the procedure of engaging the bone fastener to the bony segment since the device may obstruct the fastener insertion location. Also, such devices may not provide a readily discernable indication to the surgeon that the device is properly positioned relative to the bone plate.

SUMMARY

The present invention provides a guide assembly for positioning bone engaging fasteners at a desired position and/or orientation for securement to a bone plate. The guide assembly can include a guide member having an extension that readily interfaces with a plate or bony structure below a plate to facilitate preparation of the bony segment to receive a bone engaging fastener and/or to facilitate in the engagement of the bone engaging fastener to the bony segment.

According to one aspect of the invention, a system is provided that includes a plate positionable adjacent a bony segment and a guide assembly. The guide assembly includes at least one guide member including a guide tube having a passage therethrough extending between a distal end and a proximal end of the guide tube. The guide member further includes an extension extending distally from the guide tube. The extension is contactable with at least one of the plate and the bony segment proximate a fastener hole of the plate such that the passage is aligned with the fastener hole and the distal end of the guide tube is spaced from a proximal surface of the plate.

According to another aspect of the invention, a system is provided that includes a plate positionable adjacent a bony segment and a guide assembly. The guide assembly includes a first and second guide tubes, each having a passage therethrough extending between a distal end and a proximal end thereof. Each of the first and second guide tubes includes an extension extending distally therefrom. Each of the extensions is contactable with at least one of the plate and the bony segment proximate respective first and second fastener holes of the plate with the passages of the first and second guide tubes aligned with the respective first and second fastener holes and the distal ends of the first and second guide tubes spaced from a proximal surface of the plate.

According to another aspect of the invention, there is provided a guide assembly for securing one or more bone engaging fasteners to a bony segment relative to a plate. The guide assembly includes at least one guide tube having a passage therethrough extending between and opening at a distal end and a proximal end of the guide tube. A handle assembly extends proximally from the at least one guide tube, and an extension extends distally from the distal end of the at least one guide tube. The extension is contactable with at least one of the plate and the bony segment proximate a fastener hole through the plate with the passage aligned with the fastener hole and the distal end of the guide tube spaced from the plate.

According to another aspect of the invention, a method for securing a bone plate to a vertebra of the spinal column is provided. The method includes placing the bone plate on the vertebra with at least one hole of the bone plate aligned with the vertebra; providing a guide assembly including a guide tube with a passage opening at a distal end thereof and an extension extending distally from the guide tube; contacting at least one of the bone plate and the vertebra with the extension proximate the at least one hole and the distal end of the guide tube spaced from the bone plate; positioning a bone engaging fastener through the passage of the guide tube; and engaging the bone engaging fastener in the at least one hole of the bone plate with the vertebra.

These and other aspects of the invention will also be apparent from the following description.

DESCRIPTION OF THE ILLUSTRATED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the illustrated devices, and any further applications of the principles of the invention as illustrated herein, are contemplated as would normally occur to one skilled in the art to which the invention relates.

Figure 1:
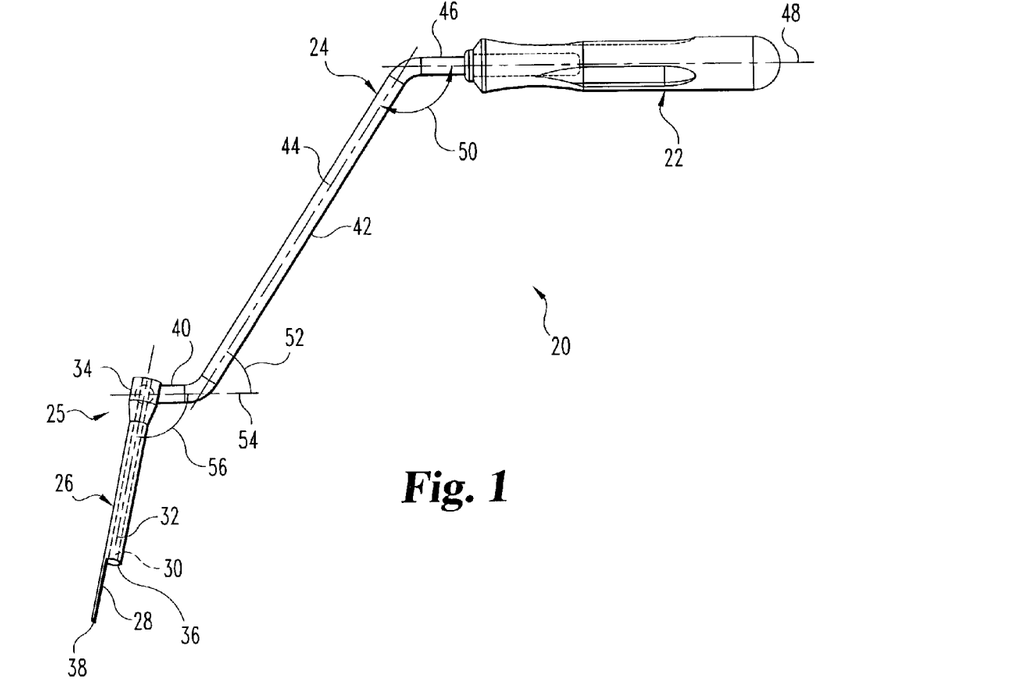
FIG. 1 is a side elevational view of a guide assembly for guiding bone engaging fasteners into a bony segment.
Figure 2:
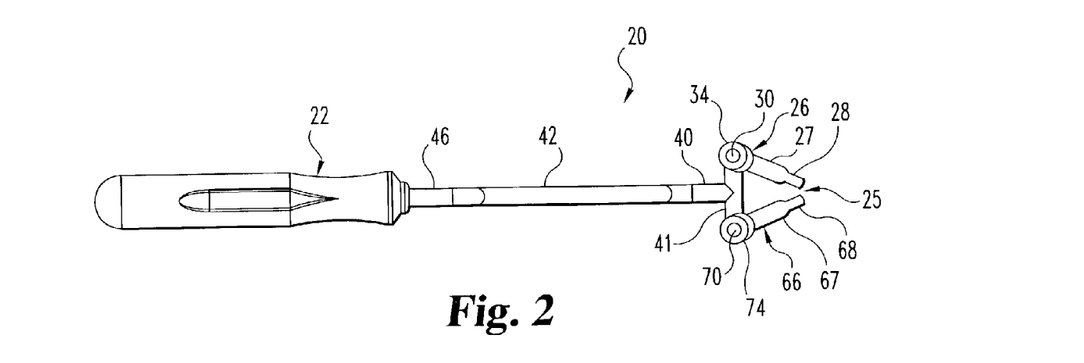
FIG. 2 is a top plan view of the guide assembly of FIG. 1.
Figure 3:
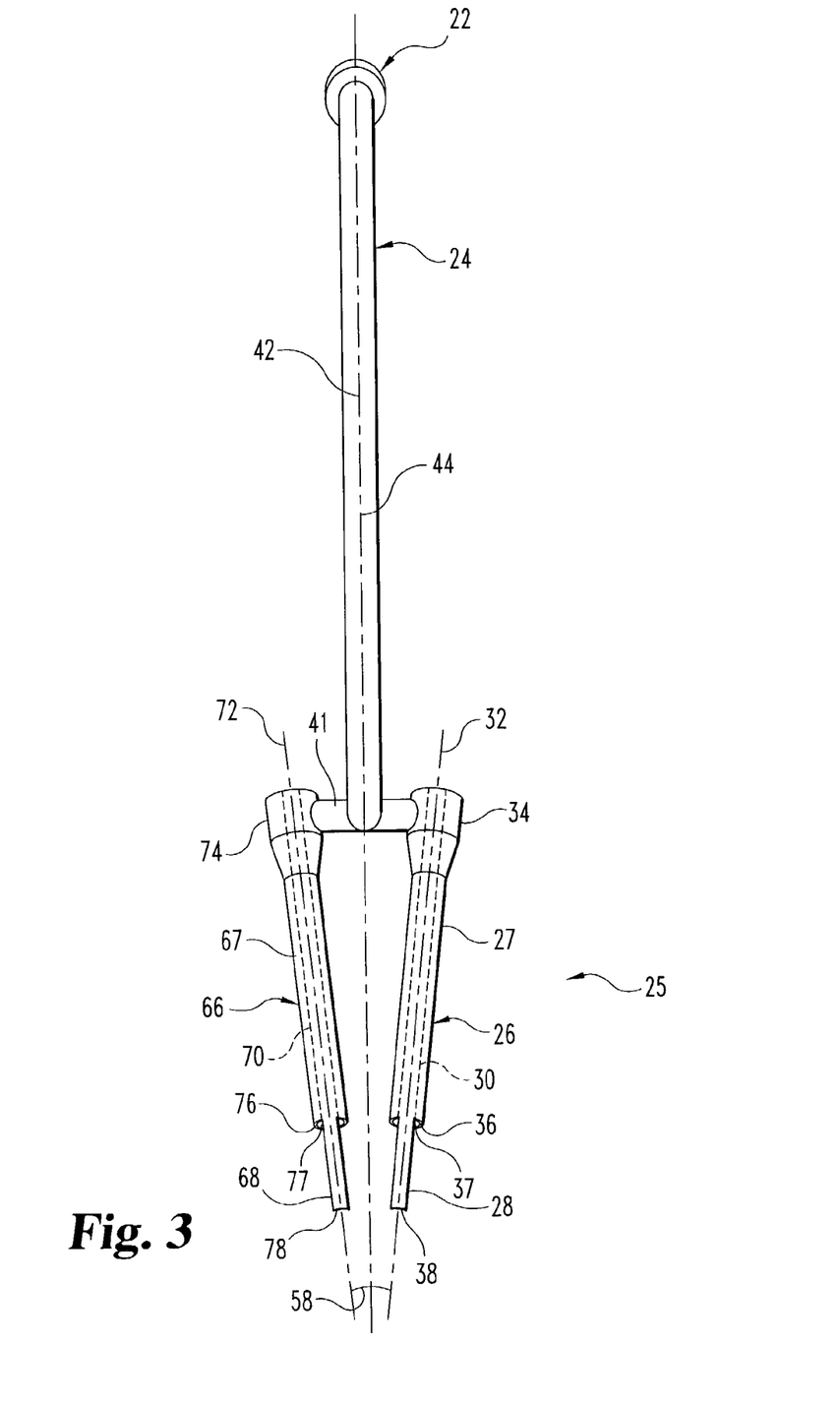
FIG. 3 is a front elevational view of the guide assembly of FIG. 1.

Referring to FIGS. 1-3, there is shown a guide assembly 20 having application in surgical techniques for securing a bone plate to a bony segment. Guide assembly 20 can be used in any one or combination of drilling one or more holes in the bony segment through a plate, such as a bone plate or a template, tapping one or more holes in the bony segment through the bone plate or template, and engaging bone engaging fasteners to the bony segment to secure the bone plate thereto. Guide assembly 20 can have application in spinal plating systems, including anterior cervical plates, thoracic plates, lumbar plates and sacral plates. Guide assembly 20 can have application with plates secured to the anterior, lateral, posterior, postero-lateral and antero-lateral aspects of the vertebrae. Guide assembly 20 can also have application in plating systems other than spinal plating systems.

Guide assembly 20 includes a proximal handle assembly 24 and a distal guide portion 25. Handle assembly 24 includes a handle 22 coupled to a shaft 42. Guide assembly 20 includes a distal guide portion 25 extending distally from handle assembly 24. Guide portion 25 includes a first guide member 26 and a second guide member 66. First guide member 26 includes a first guide tube 27 and a first extension 28 extending distally from a distal end 36 of first guide tube 27. Second guide member 66 includes a second guide tube 67 and a second extension 68 extending distally from a distal end 76 of second guide tube 67.

First guide member 26 and second guide member 66 can be connected to one another by a connecting member 41 adjacent proximal ends 34, 74 of guide members 26, 66. First guide member 26 includes a passage 30 extending through guide tube 27 and opening at proximal end 34 and distal end 36 thereof. Second guide member 66 includes a passage 70 extending through guide tube 67 and opening at proximal end 74 and distal end 76 thereof. Guide tube 27 can be centered about longitudinal axis 32, and guide tube 67 can be centered about longitudinal axis 72. It is further contemplated that first extension 28 extends along and is offset to one side of longitudinal axis 32, and second extension 68 extends along and is offset to one side of longitudinal axis 72. In the illustrated embodiment, extensions 28, 68 are offset opposite handle assembly 24 relative to guide tubes 27, 67. Other embodiments contemplate that extensions 28, 68 could be offset relative to guide tubes 27, 67 on the same side as handle assembly 24, or offset laterally relative to guide tubes 27, 67, or offset medially relative to guide tubes 27, 67.

Extensions 28, 68 are contactable with the plate and/or the bony structure beneath the plate proximate the fastener hole locations in the plate to orient and align passages 30, 70 of guide tubes 27, 67 relative to the fastener holes while guide assembly 20 is in use. Passages 30, 70 can be sized to receive at least a distal portion of a drill therethrough and guide the drill bit to its proper position and orientation through a fastener hole in a plate or a plate template. Passages 30, 70 can also receive at least a distal portion of a tap therethrough and guide the tap to its proper position and orientation through a hole formed in the bony structure with a drill bit. With distal end 36 of guide tube 27 and distal end 76 of guide tube 67, extensions 28, 68 are positioned proximate respective fastener holes of the plate such that fastener holes remain substantially unobstructed by the respective extensions 28, 68. This allows bone engaging fasteners to be guided by guide tubes 27, 67 into the plate holes while extensions 28, 68 maintain contact with the plate.

Longitudinal axes 32, 72 can be oriented such that the bone engaging fasteners positioned with guide tubes 27, 67 converge distally of guide tubes 27, 67 in the bony segment at an angle 58. In one specific embodiment, angle 58 can be about 12 degrees; however, other convergence angles 58 ranging from about 1 degree up to 180 degrees are also contemplated. It is further contemplated that guide members 26, 66 can be configured so that longitudinal axes 32, 72 diverge away from one another in the bony segment, or that longitudinal axes 32, 72 extend parallel to one another in the bony segment.

Handle assembly 24 includes a distal offset member 40 extending between connecting member 41 and shaft 42. Shaft 42 can extend proximally from offset member 40 such that its central axis 44 is centered between guide members 26, 66. Offset member 40 includes a central axis 54 that can form an angle 52 with central axis 44 of shaft 42. Handle assembly 24 further includes a proximal portion 46 extending from shaft 42 that has a central axis 48 forming angle 50 with central axis 44 of shaft 42. Handle assembly 24 can further include a handle 22 coupled to or formed with proximal portion 46.

Angles 50 and 52 can be selected to provide the surgeon clear access to insert tools, fasteners and the like through the proximal end openings of passages 30, 70 of guide tubes 27, 67, respectively. In one specific embodiment of guide assembly 20, angle 52 can be about 58 degrees and angle E4 can be about 122 degrees. Other embodiments contemplate other values for angle 52 ranging from 90 degrees or more to about 10 degrees, and values for angle 50 ranging from about 90 degrees or less to about 170 degrees. It is also contemplated that shaft 42 need not be centered between guide members 26, 66, and also could extend laterally from one of the guide members 26, 66.

Other configurations for handle assembly 24 are also contemplated. For example, in the view of FIG. 1, shaft 42 could extend substantially parallel to guide members 26, 66, or could extend along or in the direction of the plate positioned adjacent to the bony segment.

In another configuration, handle 22 could be provided along shaft 42. In a further configuration, shaft 42 could extend from connecting portion 41. Other variations in handle assembly 24 are contemplated that are suitable for positioning guide members 26, 46 adjacent a bone plate or template in the patient's body.

Longitudinal axes 32, 72 of guide members 26, 46 can be oriented relative to central axis 54 of offset portion 40 by an angle 56. Angle 56 can range from 10 degrees to about 90 degrees depending on the desired orientation of guide portion 25 relative to the handle assembly 24. For example, in one specific application where the plate is a spinal bone plate, angle 56 can be about 102 degrees to facilitate placement of the bone engaging fasteners at a 12 degree cephalad or caudal orientation relative to the plate. Other configurations are also contemplated, including configurations where guide portion 25 is connected with shaft 42, and orientations in which axes 32, 72 extend perpendicular to or at an angle relative to axis 48 of handle 22.

Figure 4:
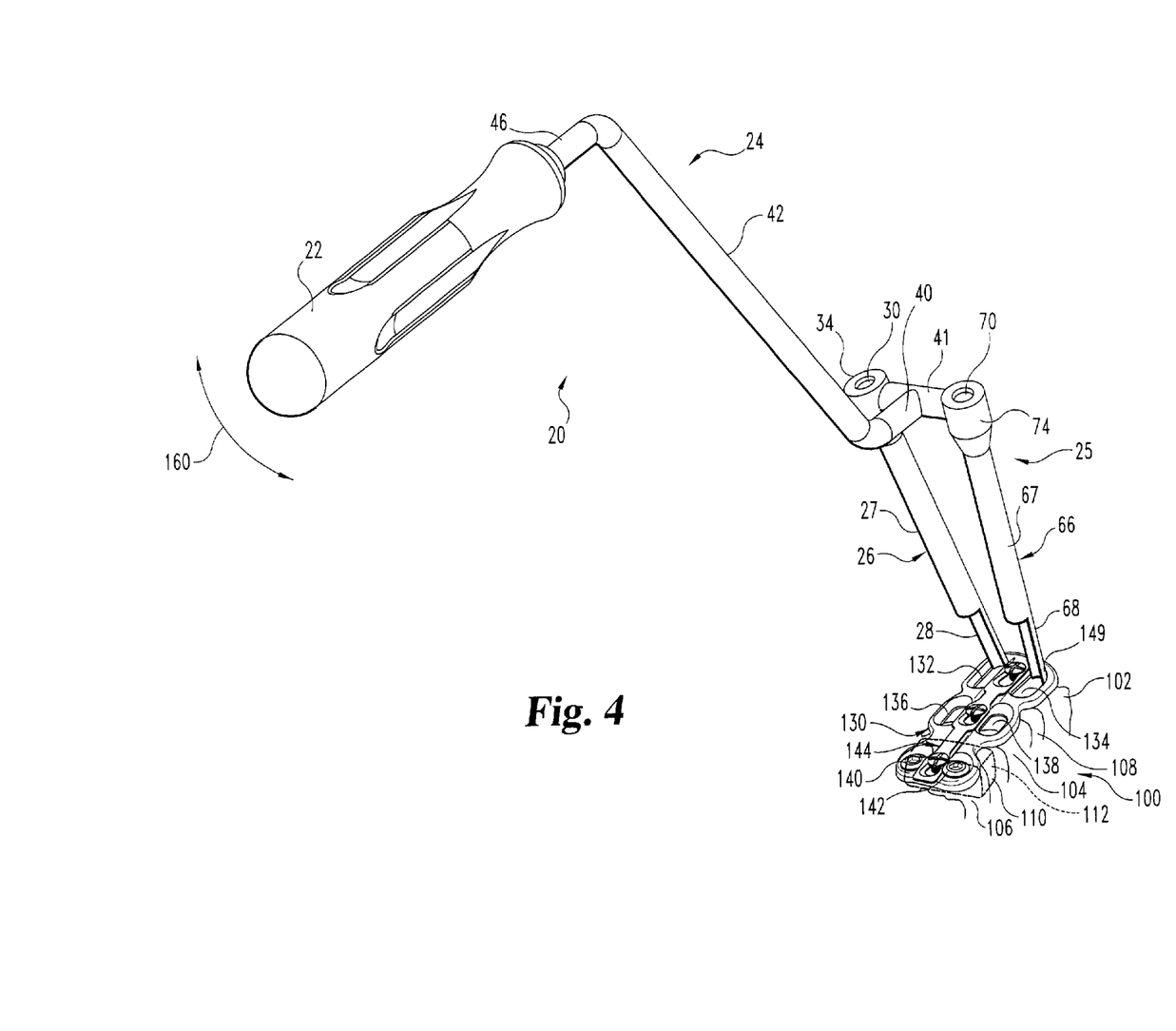
FIG. 4 is a perspective view of the guide assembly of FIG. I and a plate positioned along a spinal column segment.
Figure 5:
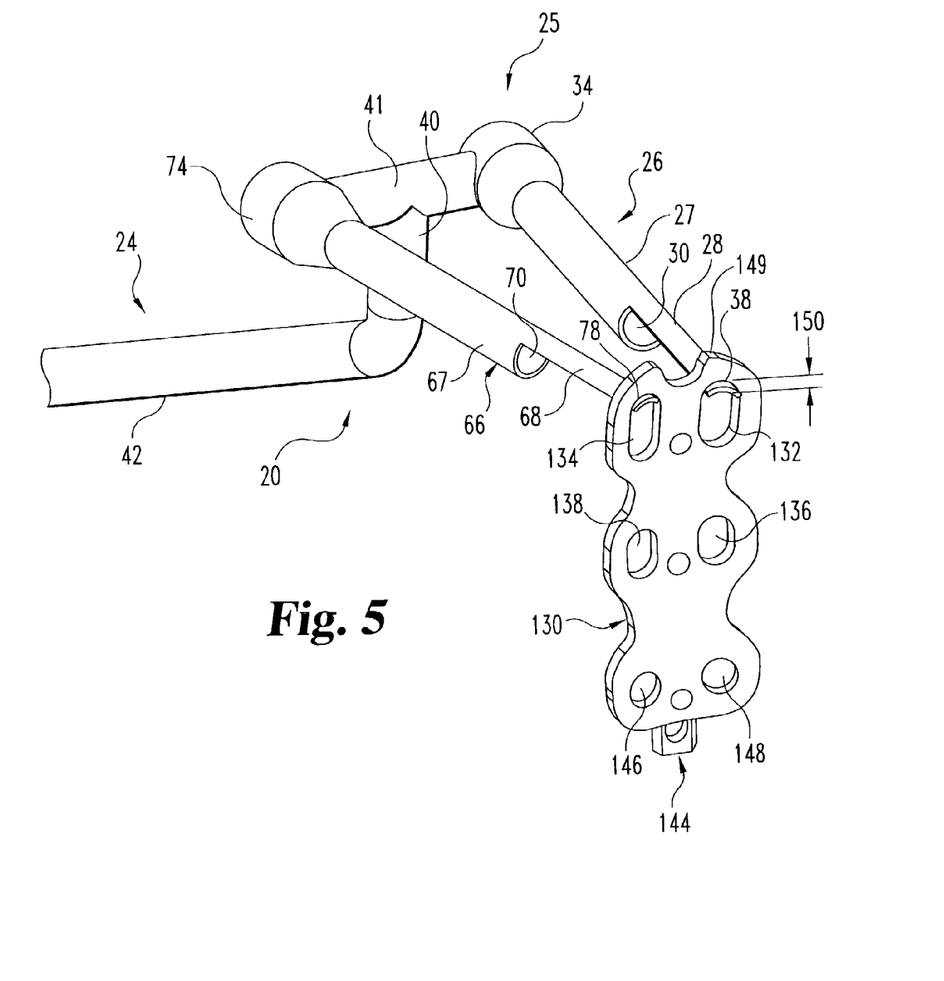
FIG. 5 is a perspective view of the guide assembly and plate of FIG. 4 looking toward the bottom of the plate.

Referring now to FIGS. 4 and 5, one specific application of guide assembly 20 with a plate along a spinal column segment will be discussed. In FIG. 4 there is shown a spinal column segment 100 having a first vertebra 102, a second vertebra 104, and a third vertebra 106. A first disc space 108 is located between first and second vertebrae 102 and 104, and a second disc space 110 is located between second and third vertebrae 104 and 106. In procedures where fusion of adjacent vertebrae is desired, an implant, such as implant 112, can be positioned in one or both of the spinal disc spaces 108, 110.

To stabilize spinal column segment 100, or to provide a template to guide the location of the bone engaging fasteners relative to the vertebrae, a plate 130 can be positioned along any one or all of the vertebrae 102, 104, 106. Plate 130 includes a first pair of holes 132, 134 aligned with first vertebra 102, a second pair of holes 136, 138 aligned with second vertebra 104, and a third pair of holes 146, 148 (FIG. 5) aligned with third vertebra 106. Bone engaging fasteners, such as fasteners 142, 144, can be positioned through any one or combination of the holes with guide assembly 20 to secure plate 130 to spinal column segment 100 or to properly position the bone engaging fasteners relative to plate 130 for engagement with a bone plate.

It should be understood that plate 130 could be a bone plate, as shown, or a template. Plate 130 could be configured to span one, two, or three or more vertebrae. It is also contemplated that only a single hole in the plate can be provided at any one or all of the vertebrae, or that three or more holes can be provided at any one or all of the vertebrae. A retaining assembly 144 can be provided with plate 130 in the form of a bone plate to prevent fastener back-out from the holes. Retaining assembly 144 can be associated with each of the plate holes, or associated with any subset of the plate holes. Multiple retaining assemblies could be provided so that all or less than all of the plate holes have a retaining assembly associated therewith.

It is contemplated that implant 112 could be a bone graft, interbody fusion device, artificial disc device, or other interbody implant. Such implants can be made from bone material, man-made material, or combinations thereof. In procedures where fusion of the adjacent vertebrae is desired, bone growth material and bone growth facilitators could be provided to facilitate such fusion. Any suitable osteogenetic material or composition is contemplated for placement within or around implant 112. Such osteogenic material includes, for example, autograft, allograft, xenograft, demineralized bone, synthetic and natural bone graft substitutes, such as bioceramics and polymers, and osteoinductive factors. A separate carrier to hold the materials in the disc space or in the implant can also be used. These carriers can include collagen-based carriers, bioceramic materials, such as BIOGLASS®, hydroxyapatite and calcium phosphate compositions. The carrier material can be provided in the form of a sponge, a block, folded sheet, putty, paste, graft material or other suitable form. Moreover, the osteogenetic compositions can comprise an effective amount of a bone morphogenetic protein, transforming growth factor β1, insulin-like growth factor 1, platelet-derived growth factor, fibroblast growth factor, LIM mineralization protein (LMP), and combinations thereof or other therapeutic or infection resistant agent, held within a suitable carrier material.

In use, guide assembly 20 can be positioned relative to plate 130 so that distal ends 38, 78 of extensions 28, 68 are received in receptacles in the plate. As discussed further below, it is contemplated that receptacles could be provided by holes 132, 134, provided adjacent to holes 132, 134, and/or provided in communication with holes 132, 134. Extensions 28, 68 can contact the portion of the plate surrounding or proximate to plate holes 132, 134 to locate guide assembly 20 relative to the plate, and to facilitate maintenance of the positioning of guide assembly 20 relative to plate 130. Extensions 28, 68 can alternatively or additionally contact the bony structure underlying plate 130 proximate holes 132, 134 to locate guide assembly 20 relative to plate 130, and to maintain the positioning of guide assembly 20 relative to plate 130. The orientation of longitudinal axes 32, 72 of guide tubes 27, 67 relative to plate 130 can be adjusted by manipulating handle assembly 24 as indicated by arrow 160.

In the illustrated embodiment, holes 132, 134 can be elongated along the longitudinal axis of plate 130 to provide a slotted arrangement. With extensions 28, 68 in contact with the ends of holes 132, 134, the edge of the fasteners inserted through guide tubes 27, 67 can be offset from the edge of the holes by distance 150 as shown in FIG. 5. If so offset, the inserted fasteners can move in either direction in holes 132, 134 in response to movement of the spinal column segment in compression or tension. Other embodiments contemplate other shapes for holes 132, 134, including slotted and non-slotted holes that are circular, oval, oblong, square, rectangular or other shape suitable for receiving a bone engaging fastener.

Guide assembly 20 is shown positioned at the ends of holes 132, 134 adjacent the end 149 of plate 130. Guide assembly 20 could be positioned to locate extensions 28, 38 adjacent the opposite ends of holes 132, 134. Guide assembly 20 could be used to drill holes through holes 132, 134 into vertebra 102, and also to tap the drilled holes. Once the holes are drilled and, if desired, tapped into vertebra 102, bone engaging fasteners can be guided through guide tubes 27, 67 and into the drilled and tapped holes. It is also contemplated that guide tubes 27, 67 could be used to guide self-tapping bone screws or fasteners into vertebra 102, or to guide self-drilling bone screws or fasteners into vertebra 102, without drilling and/or tapping the bony structure. The procedure can then be repeated at each vertebra 104, 106 to secure bone engaging fasteners thereto. Guide members 26, 66 can have a length or other configuration selected to interact with the drilling, tapping, and/or fastener driver instrument to limit the depth of penetration into the vertebral body. For example, the instruments can contact the proximal ends of guide members 26, 66, or contact an internal stop surface provided in passages 30, 70 to limit the penetration depth.

Figure 6:
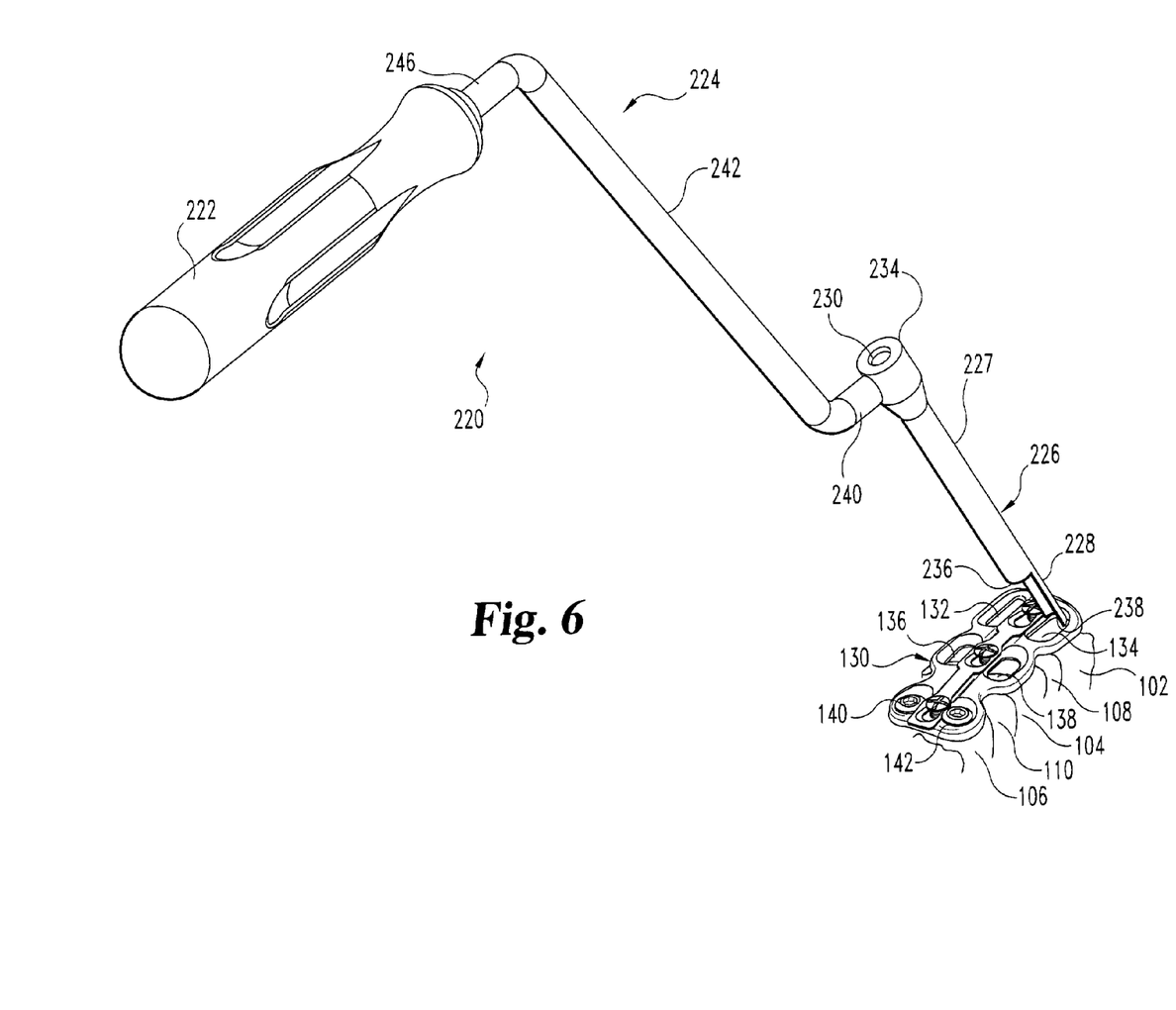
FIG. 6 is a perspective view of another embodiment guide assembly and a plate positioned along a spinal column segment.

Another embodiment guide assembly is shown in FIG. 6. Guide assembly 200 includes a proximal handle assembly 224 and a distal guide portion 225. Handle assembly 224 includes a shaft 242 having a proximal portion 246 extending therefrom. A handle 222 is coupled to or formed with proximal portion 246. A distal extension 240 extends from a distal end of shaft 242 and is coupled or formed with guide portion 225. Guide portion 225 includes a guide member 226. Guide member 226 includes a guide tube 227 and an extension 228 extending distally from a distal end 236 of guide tube 227. Guide tube 227 includes a passage 230 opening at a proximal end 234 of guide tube 227 and also opening at distal end 236 of guide tube 227.

Guide assembly 200 includes a single guide member 226 configured to receive and guide instruments for the drilling of and, if desired, tapping of holes in respective ones of the vertebrae 102, 104, 106 of spinal column segment 100 through holes in plate 130. Distal end 236 of guide member 227 is spaced from plate 130, and passage 230 can be sized to allow passage of a bone screw or other bone engaging fastener therethrough for guided placement and engagement of the bone engaging fastener to the respective vertebra. Guide assembly 200 can be repositioned proximate each of or selected ones of the receptacles provided by the holes or adjacent to the holes through plate 130 to prepare each vertebra to receive and to secure a bone engaging fastener thereto. A distal end 238 of extension 228 can contact the plate in a receptacle provided by or adjacent to a plate hole and/or contact the bony structure underlying plate 130 to position and maintain the position of guide assembly 200 proximate the plate hole during drilling, tapping, and/or fastener insertion.

Figures 7, 8, 9, 10:
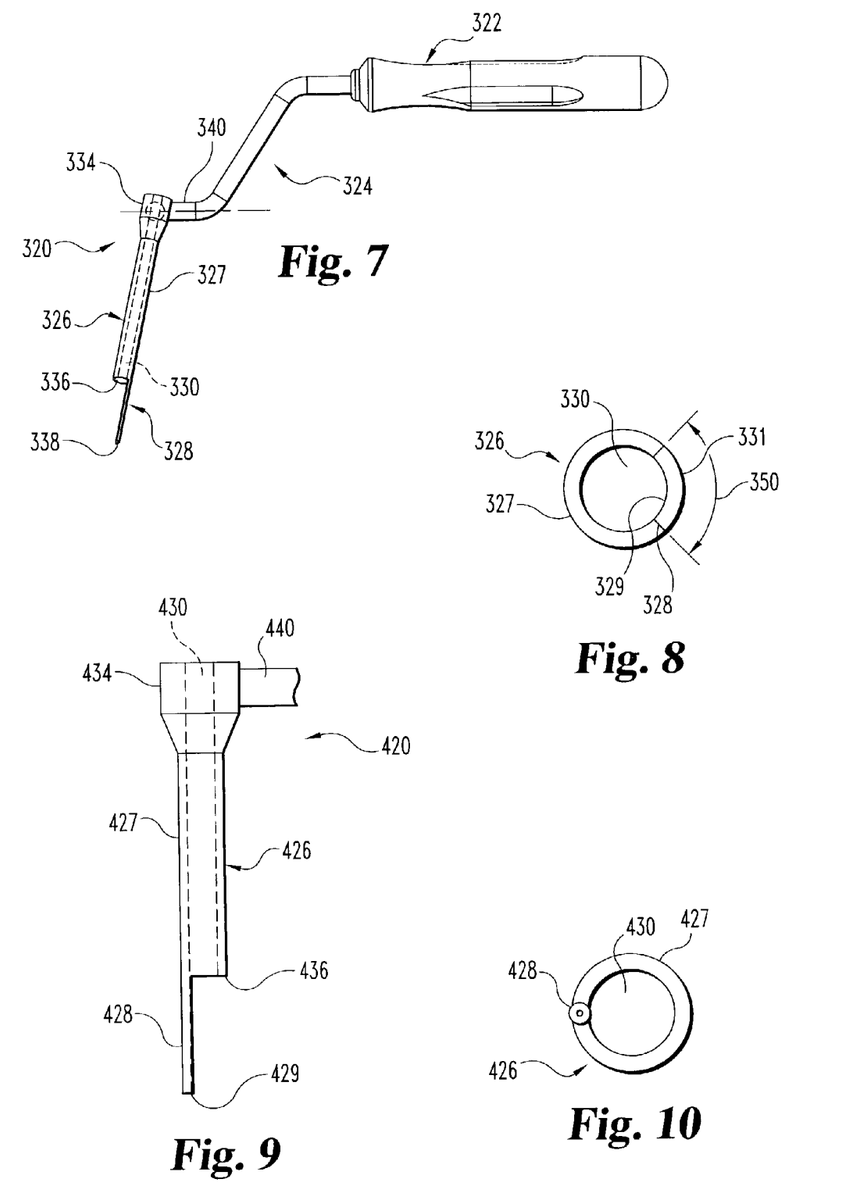
FIG. 7 is an elevational view of a distal portion of another embodiment guide assembly.
FIG. 8 is a distal end view of the distal portion of FIG. 7.
FIG. 9 is an elevational view of a distal portion of another embodiment guide assembly.
FIG. 10 is a distal end view of the distal portion of FIG. 9.

In FIG. 7 there is shown another embodiment guide assembly 320 having a proximal handle assembly 324 with a handle 322 and a shaft 340. A guide member 326 extends distally from shaft 340. Guide member 326 includes at least one guide tube 327 and an extension 328 extending distally from guide tube 327. A passage 330 extends through and opens at a proximal end 334 and a distal end 336 of guide tube 327. In this embodiment, extension 328 extends from guide tube 327 along the same side of guide tube 327 from which handle assembly 324 extends. In the embodiments illustrated above, the extensions are shown extending from the side of the guide tube opposite the side from which handle assembly extends. It is also contemplated that the extension could extend from a side of the guide tube laterally oriented with respect to the guide tube.

In FIG. 8 an end view of the guide member 326 is provided. Extension 328 can be provided with a width 350 along the perimeter of guide tube 327 that is less than the perimeter of guide tube 327. It is contemplated in one embodiment that width 350 can range from about 1 percent to about 95 percent of the perimeter of guide tube 327. In a further embodiment, width 350 can range from about 5 percent to about 50 percent of the perimeter of guide tube 327. In another embodiment, width 350 can range from about 5 percent to about 35 percent of the perimeter of guide tube 327. In a further embodiment, width 350 can range from about 5 percent to about 25 percent of the perimeter of guide tube 327. The other embodiment guide assemblies discussed herein can be similarly provided with an extension having a length that occupies similar portions of the perimeter of the guide tube from which it extends.

Extension 328 can be provided with an inner surface 329 that forms an extension of a portion of the inner surface defining passage 330. In the illustrated embodiment, inner surface 329 is a concave surface and opposite outer surface 331 is a convex surface extending to a distal end 338. Inner surface 329 can guide bone engaging fasteners, drills, taps and the like positioned through passage 330. Outer surface 331 can nest against a correspondingly shaped surface of the receptacle in which it is placed. The extensions of the other guide assembly embodiments discussed herein can also be similarly configured to guide the placement of bone engaging fasteners, drills, taps and the like positioned through the passage of the guide tube from which the extensions extend.

In FIG. 9, there is shown another embodiment guide assembly 420 having a proximal handle assembly with shaft 440 and a handle (not shown.) A guide member 426 extends distally from shaft 440. Guide member 426 includes at least one guide tube 427 and an extension 428 extending distally from guide tube 427. A passage 430 extends through and opens at a proximal end 434 and a distal end 436 of guide tube 427. In this embodiment, extension 428 is in the form of a pin that extends distally from guide tube 427. As shown in FIG. 10, extension 428 can have a circular cross-section and a pointed distal end 429 for embedding in or engaging the bony structure against which it is positioned. Accordingly, the positioning of guide assembly 420 can be maintained by contact with the bony structure in addition to or in lieu of contact with the plate by extension 428.

It is contemplated that extension 428 and/or the extensions of the guide assemblies discussed above could be integral with the guide tube from which the extension extends. It is also contemplated that the extensions could be attached to the guide tubes by any one or combination of a threaded connection, bolted connection, riveted connection, welded connection, bayonet lock, clamp, or other suitable attachment arrangement. It is contemplated that each guide tube could be provided with multiple extensions extending distally therefrom.

Figure 11:
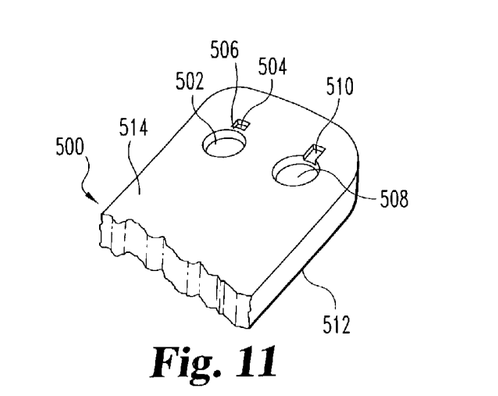
FIG. 11 is a perspective view of a portion of a bone plate having various receptacle configurations.
Figure 12:
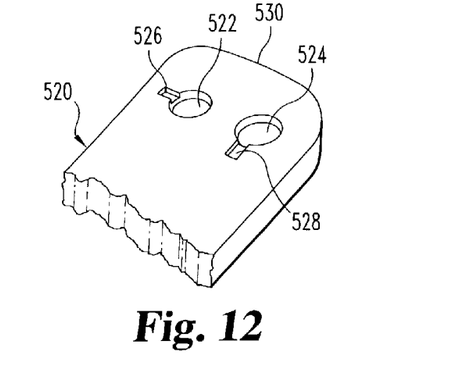
FIG. 12 is a perspective view of a portion of a bone plate having various receptacle configurations.

In FIGS. 11 and 12, there are shown other arrangements for receptacles in the bone plates or template plates useable with at least some of the guide assembly embodiments discussed herein. In the embodiments discussed above, the plate hole provides the receptacle proximate the hole in which the extension can be positioned to contact the plate and/or the underlying bony structure. In FIG. 11, plate 500 includes a hole 502 extending between and opening at a proximal surface 514 and a distal surface 512 of plate 500. A receptacle 504 is formed in proximal surface 514 proximate hole 502. Receptacle 504 can extend partially into or completely through plate 500. Receptacle 504 is spaced from hole 502 by a plate segment 506. The guide assembly extension is positionable in receptacle 504 to orient the passage of the guide tube from which the extension extends in alignment with hole 502.

Another embodiment receptacle is shown in plate 500 of FIG. 11 proximate hole 508. Plate 500 includes a receptacle 510 in communication with hole 508. Receptacle 510 can open at proximal surface 514 and can extend partially or completely through plate 500. An extension of the guide assembly is positionable in receptacle 510 in contact with plate 500 to orient the passage of the guide tube from which the extension extends in alignment with hole 508.

FIG. 12 shows plate 520 in which holes 522, 524 are provided with receptacles 526, 528, respectively, proximate thereto. Receptacle 526 is oriented laterally in the plate with respect to hole 522 toward the outer edge of the plate 520. Other embodiments contemplate that receptacle 526 could be oriented medially with respect to hole 522. With respect to hole 524, receptacle 528 is oriented away from the end 530 of plate 520. Other orientations of the receptacles relative to the plate holes are also contemplated.

Various configurations for the extension relative to the guide tube of the guide assemblies are also contemplated. For example, in FIG. 13 there is a guide member 550 for a guide assembly. Guide member 550 includes a guide tube 552 having a passage 554 extending therethrough and opening at a distal end 556 of guide tube 552. Extension 558 extends distally from distal end 556. The walls of guide tube 552 have a first thickness 560, and extension 558 has a second thickness 562. In one embodiment, second thickness 562 can be less than thickness 560. The reduced thickness of extension 558 facilitates its positioning in, for example, receptacle 504 of plate 500 while passage 554 is aligned with hole 502. Extension 558 could also be positioned in, for example, receptacle 510 of plate 500 while passage 554 is aligned with hole 508 of plate 500. Extension 558 could also be positioned in receptacles provided by the holes of the plate, such as shown with plate 130.

Figure 13:
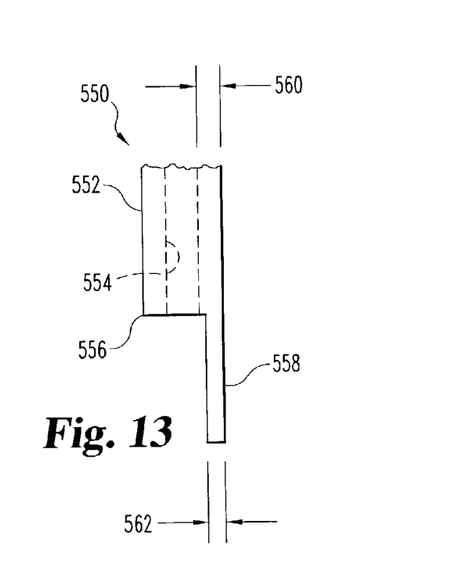
FIG. 13 is an elevation view of another embodiment guide tube comprising a portion of a guide assembly.

Extension 558 is offset from a projection of passage 554 of guide tube 552 along extension 558. The offset can minimize interference of the extension with the bone engaging fastener as the bone engaging fastener positioned in the plate hole. Other embodiments contemplate extensions having a thickness that is the same or about the same as thickness of the wall of the guide tube.

Figure 14:
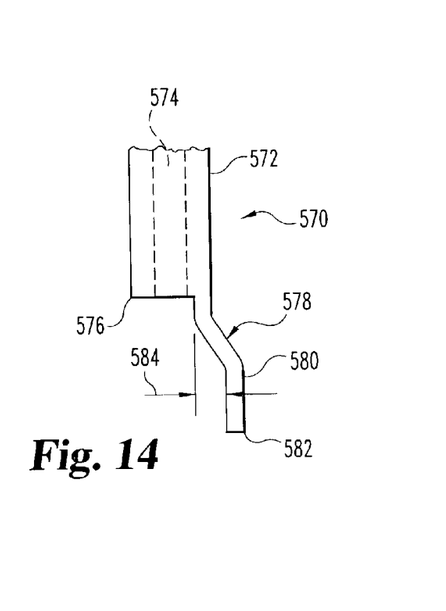
FIG. 14 is an elevation view of another embodiment guide tube comprising a portion of a guide assembly.

In FIG. 14 there is another embodiment guide member 570 for a guide assembly. Guide member 570 includes a guide tube 572 having a passage 574 extending therethrough and opening at a distal end 576 of guide tube 572. Extension 578 extends distally from distal end 576. Extension 578 can be provided with an offset portion 580 at any location therealong such that distal end 582 is positioned away from passage 574 by distance 584. Extension 578 is thus offset from a projection of the passage of the guide tube along the extension. Extension 578 could be positioned in, for example, receptacle 504 of plate 500 while passage 574 is aligned with hole 502 of plate 500. Extension 578 could also be positioned in, for example, receptacle 510 of plate 500 with passage 574 aligned with hole 508 of plate 500. Extension 578 could also be positioned in receptacles provided by the holes of the plate, such as shown with plate 130.

While the invention has been illustrated and described in detail in the drawings and foregoing description, the same is to be considered as illustrative and not restrictive in character, and that all changes and modifications the come within the spirit of the invention are desired to be protected.

What is claimed is:

1. A system, comprising:
   a plate positionable adjacent a bony segment, said plate including at least one fastener hole therethrough extending between a proximal surface and a distal surface of said plate, wherein said plate is elongated and extends along a longitudinal axis between an upper end positionable over a first vertebra and an opposite lower end positionable over a second vertebra and said at least one fastener hole includes a first end oriented toward said upper end of said plate and a second end oriented toward said lower end of said plate; and
   a guide assembly comprising at least one guide member including a guide tube having a passage therethrough extending between and opening at a most distal end and a proximal end of said guide tube, said guide tube further including a single extension extending distally from said most distal end of said guide tube along a side of said passage, wherein said extension contacts said plate at one of said first and second ends of said at least one fastener hole with said passage aligned with said at least one fastener hole and said most distal end of said guide tube spaced from said proximal surface of said plate.

2. The system of claim 1, wherein said at least one fastener hole is a slot elongated in the direction of a longitudinal axis of said plate from said first end to said second end of said at least one fastener hole.

3. The system of claim 2, wherein said slot forms a receptacle in which said extension is positioned.

4. The system of claim 2, wherein said extension is positioned in said at least one fastener hole against said first end of said slot when said extension is in contact with said plate.

5. The system of claim 1, wherein said extension is positioned in a receptacle in said plate in communication with said at least one fastener hole when said extension is in contact with said plate.

6. The system of claim 1, wherein said extension includes an inner surface that forms an extension of said passage of said guide tube and an opposite outer surface, said outer surface including a convex curvature configured to nestingly engage a correspondingly shaped surface of said at least one fastener hole.

7. The system of claim 1, wherein said extension includes a distal end pointed for penetrating the bony segment.

8. The system of claim 1, wherein said extension includes an inner surface extending from said most distal end of said guide tube that is aligned with a projection of said passage along said extension and said extension further includes an offset portion that spaces said inner surface a distance from said projection of said passage.

9. The system of claim 1, wherein said passage of said guide tube is sized to receive a bone engaging fastener therethrough for engagement to the bony segment through said at least one hole when said extension is in contact with at least one of said plate and the bony segment.

10. The system of claim 1, wherein said extension includes a concave surface oriented toward said passage and a convex surface opposite said concave surface.

11. The system of claim 1, wherein said guide tube includes a perimeter and said extension includes a width along said perimeter, said width being in the range from about 1 percent to about 50 percent of said perimeter.

12. The system of claim 1, wherein said guide tube includes a perimeter and said extension includes a width along said perimeter, said width being in the range from about 5 percent to about 25 percent of said perimeter.

13. The system of claim 1, wherein said extension is integral with said guide tube.

14. The system of claim 1, wherein said extension includes a guide surface extending therealong oriented toward said passage.

15. The system of claim 1, wherein said guide assembly further comprises a second guide member including a second guide tube including a second passage therethrough extending between a distal end and a proximal end of said second guide tube, said second guide member further including a single second extension extending distally from said second guide tube, wherein said plate includes a second fastener hole including a first end oriented toward said upper end of said plate and an opposite second end located toward said lower end of said plate, said second extension contacts said plate at one of said first and second ends of said second fastener hole with said second passage aligned with said second fastener hole and said distal end of said second guide tube spaced from said proximal surface of said plate.

16. The system of claim 1, further comprising an implant positionable in the bony segment.

17. The system of claim 16, further comprising bone growth material positionable in the bony segment with said implant.

18. The system of claim 1, wherein said guide assembly includes a handle assembly extending proximally from said guide tube.

19. The system of claim 1, wherein said plate is selected from the group consisting of: a bone plate and a template.

20. The system of claim 1, wherein said extension is attached directly to said guide tube and wherein said extension contacts said plate in said at least one fastener hole to align said passage with said at least one fastener hole while said most distal end of said guide tube is spaced from said proximal surface of said plate.

21. The system of claim 20, wherein said passage opens at said end of said guide tube and said extension extends distally from said opening of said passage.

22. The system of claim 1, wherein said guide tube includes an inner surface that extends around said passage and said passage opens at said most distal end of said guide tube and said extension includes a concavely curved inner surface that forms an extension of a portion of said inner surface of said guide tube, wherein said inner surface of said extension extends distally from said opening of said passage and said inner surface includes a width around said most distal end of said guide tube that is less than a perimeter of said inner surface around said passage of said guide tube.

23. A system, comprising:
   a plate positionable adjacent a bony segment, said plate including at least a first fastener hole and a second fastener hole extending therethrough between a proximal surface and a distal surface of said plate, wherein said plate is elongated and extends along a longitudinal axis between an upper end positionable over a first vertebra and an opposite lower end positionable over a second vertebra and said first and second fastener holes each include a first end oriented toward said upper end of said plate and a second end oriented toward said lower end of said plate;

a guide assembly comprising:

a first guide tube including a passage therethrough extending between and opening at a most distal end and a proximal end of said first guide tube, a single first extension extending distally from said most distal end of said first guide tube along a side of said passage, wherein said single first extension contacts said plate at one of said first and second ends in said first fastener hole with said first passage aligned with said first fastener hole and said distal end of said first guide tube spaced from said proximal surface of said plate; and a second guide tube including a second passage therethrough extending between and opening at a most distal end and a proximal end of said second guide tube, a single second extension extending distally from said most distal end of said second guide tube, wherein simultaneously with said single first extension contacting said plate in said first fastener hole said second extension contacts said plate with said second extension at one of said first and second ends in said second fastener hole with said second passage aligned with said second fastener hole and said distal end of said second guide tube spaced from said proximal surface of said plate.

24. The system of claim 23, wherein said guide assembly further comprises a handle assembly extending proximally from said first and second guide tubes.

25. The guide assembly of claim 23, wherein each of said guide tubes includes a longitudinal axis extending through said passage thereof, said longitudinal axes converging toward one another distally of said distal ends of said guide tubes.

26. The system of claim 23, wherein each of said first and second fastener holes are elongated between said first and second ends thereof in the direction of said longitudinal axis of said plate and each of said first and second extensions are positionable simultaneously in respective ones of said first and second fastener holes in contact with said plate at said corresponding one of said first and second ends of said first and second fastener holes.

27. The system of claim 26, wherein each of said first and second passages are sized for receipt of a bone engaging fastener therethrough for positioning said bone engaging fasteners in corresponding ones of said elongated first and second fastener holes.

28. The system of claim 23, wherein said first extension is attached directly to said first guide tube and said second extension is attached directly to said second guide tube and wherein said first and second extensions each contact said plate in said respective ones of said first and second fastener holes to align said passages of said first and second guide tubes with said respective ones of said first and second fastener holes while said most distal end of said first and second guide tubes are spaced from said proximal surface of said plate.

29. The system of claim 23, wherein:

said passage of said first guide tube opens at said distal end of said first guide tube and said first extension extends distally from said opening of said passage of said first guide tube;

said passage of said second guide tube opens at said distal end of said second guide tube and said second extension extends distally from said opening of said passage of said second guide tube; and at least one of said first and second guide tubes includes an inner surface that extends around said passage thereof and said passage thereof opens at said most distal end of said at least one of said first and second guide tubes, said extension of said at least one of said first and second guide tubes including a concavely curved inner surface that forms an extension of a portion of said inner surface of said at least one of said first and second guide tubes, wherein said inner surface of said extension extends distally from said opening of said passage and said inner surface includes a width around said most distal end of said at least one of said first and second guide tubes that is less than a perimeter of said inner surface around said passage.

30. A system that includes a guide assembly for securing one or more bone engaging fasteners to a bony segment relative, comprising:

a bone plate including a length along a longitudinal axis sized to extend between first and second vertebrae, said bone plate including a distal surface for facing the first and second vertebrae and an opposite proximal surface, said plate further including at least one elongated slot opening at said distal and proximal surfaces, said elongated slot being elongated in the direction of the longitudinal axis;

at least one guide tube having a passage therethrough extending between and opening at a most distal end and a proximal end of said guide tube;

a handle assembly extending proximally from said at least one guide tube; and a single extension extending distally from said most distal end of said at least one guide tube, wherein said single extension contacts the plate in said elongated slot with said passage aligned with said elongated slot and said distal end spaced from the plate, wherein said extension is configured so that a bone engaging fastener guided through said passage and into said slot when said extension contacts said plate is positioned in said elongated slot for said bone engaging fastener and said plate to be movable relative to one another in both directions along said longitudinal axis.

31. The system of claim 30, wherein said handle assembly is oriented away from said proximal end of said guide tube.

32. The system of claim 30, wherein said extension includes a pointed distal end for penetrating the bony segment.

33. The system of claim 30, wherein said passage of said guide tube is sized to receive a bone engaging fastener therethrough for engagement in the hole of the plate when said guide assembly is in contact with the plate.

34. The system of claim 30, wherein said extension includes a concave surface oriented toward said passage and a convex surface opposite said concave surface.

35. The system of claim 30, wherein said guide tube has a perimeter and said extension includes a width along said perimeter, said width being in the range from about 1 percent to less than about 50 percent of said perimeter.

36. The system of claim 30, wherein said guide tube has a perimeter and said extension includes a width along said perimeter, said width being in the range from about 5 percent to less than about 25 percent of said perimeter.

37. The system of claim 30, wherein said extension is integral with said guide tube.

38. The system of claim 30, wherein said extension includes a guide surface extending therealong oriented toward said passage.

39. The system of claim 30, further comprising:
- a second guide tube coupled to said at least one guide tube, said second guide tube having a second passage therethrough extending between a distal end and a proximal end of said second guide tube; and
- a second extension extending distally from said second guide tube, wherein said second extension is contactable with at least one of the plate and the bony segment proximate a second fastener hole adjacent the fastener hole with said second passage aligned with the second fastener hole and said distal end of said second guide tube spaced from the plate.

40. The system of claim 39, wherein said handle assembly includes:
- a connecting member coupled to each of said guide tubes;
- a shaft extending proximally from said connecting member; and
- a handle at a proximal end of said shaft.

41. The system of claim 39, wherein each of said guide tubes includes a longitudinal axis extending through said passage thereof, said longitudinal axes converging towards one another distally of said guide tubes.

42. The system of claim 30, wherein said guide tube has a first wall thickness at said distal most end between an inner surface and an outer surface of said guide tube, and wherein said extension has a second wall thickness between an inner surface of said extension and an outer surface of said extension that is less than said first wall thickness and said inner surface of said extension is offset from a projection of said passage of said guide tube along said inner surface of said extension.

43. The system of claim 30, wherein said extension includes an inner surface extending from said most distal end of said guide tube that is aligned with a projection of said passage along said extension and said extension further includes an offset portion that spaces said inner surface a distance from said projection of said passage.

44. The system of claim 30, wherein said guide tube includes an inner surface that extends around said passage and said passage opens at said most distal end of said guide tube and said extension includes a concavely curved inner surface that forms an extension of a portion of said inner surface of said guide tube, wherein said inner surface of said extension extends distally from said opening of said passage and said inner surface includes a width around said most distal end of said guide tube that is less than a perimeter of said inner surface around said passage of said guide tube.

45. The system of claim 30, wherein said extension has a length such that said distal end of said guide tube is spaced a distance from a proximal surface of the plate when said extension is in contact with at least one of the plate and the bony segment.

\* \* \* \* \*

UNITED STATES PATENT AND TRADEMARK OFFICE
CERTIFICATE OF CORRECTION

PATENT NO. : 7,625,378 B2  Page 1 of 1
APPLICATION NO. : 10/261120
DATED : December 1, 2009
INVENTOR(S) : Kevin T. Foley It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 895 days.

Signed and Sealed this

Twenty-sixth Day of October, 2010

David J. Kappos
*Director of the United States Patent and Trademark Office*